United States Patent [19]

Tsukaya

[11] Patent Number: 4,509,508
[45] Date of Patent: Apr. 9, 1985

[54] ENDOSCOPE SYSTEM

[75] Inventor: Takashi Tsukaya, Tokyo, Japan

[73] Assignee: Olympus Optical Co., Ltd., Tokyo, Japan

[21] Appl. No.: 437,461

[22] Filed: Oct. 28, 1982

[30] Foreign Application Priority Data

Nov. 5, 1981 [JP] Japan .................... 56-177751

[51] Int. Cl.³ .............................................. A61B 1/06
[52] U.S. Cl. ................................... 128/6; 362/32
[58] Field of Search ............................ 128/4–8; 358/98; 362/32; 354/62

[56] References Cited

U.S. PATENT DOCUMENTS

| | | | |
|---|---|---|---|
| 4,330,189 | 5/1982 | Takayana | 354/62 |
| 4,349,014 | 9/1982 | Takamatsu | 128/6 |
| 4,356,534 | 10/1982 | Hattori | 362/32 |
| 4,403,605 | 9/1983 | Tanikawa | 128/6 |
| 4,407,272 | 10/1983 | Yanaguchi | 128/6 |

FOREIGN PATENT DOCUMENTS 0024706  3/1981  European Pat. Off. ............ 128/6

Primary Examiner—Edward M. Coven
Assistant Examiner—Max F. Hindenburg

[57] ABSTRACT

An endoscope system is provided with a lamp for illuminating a body cavity through an endoscope, and a lamp energizing circuit for adjusting current to be supplied to the lamp. Control data for controlling the lamp is stored in a ROM. While the ROM is held in an enabling state by a chip selector according to setting data from switches and a zerocross detector, the control data is read out from the ROM by a CPU, and the lamp is energized in accordance with the control data. If the ROM is not in the enabling state although the CPU is fetching the setting data and control data, then an alarm signal is delivered from a NOR gate, and the lamp is so energized as to provide a maximum brightness.

7 Claims, 24 Drawing Figures

F I G. 1
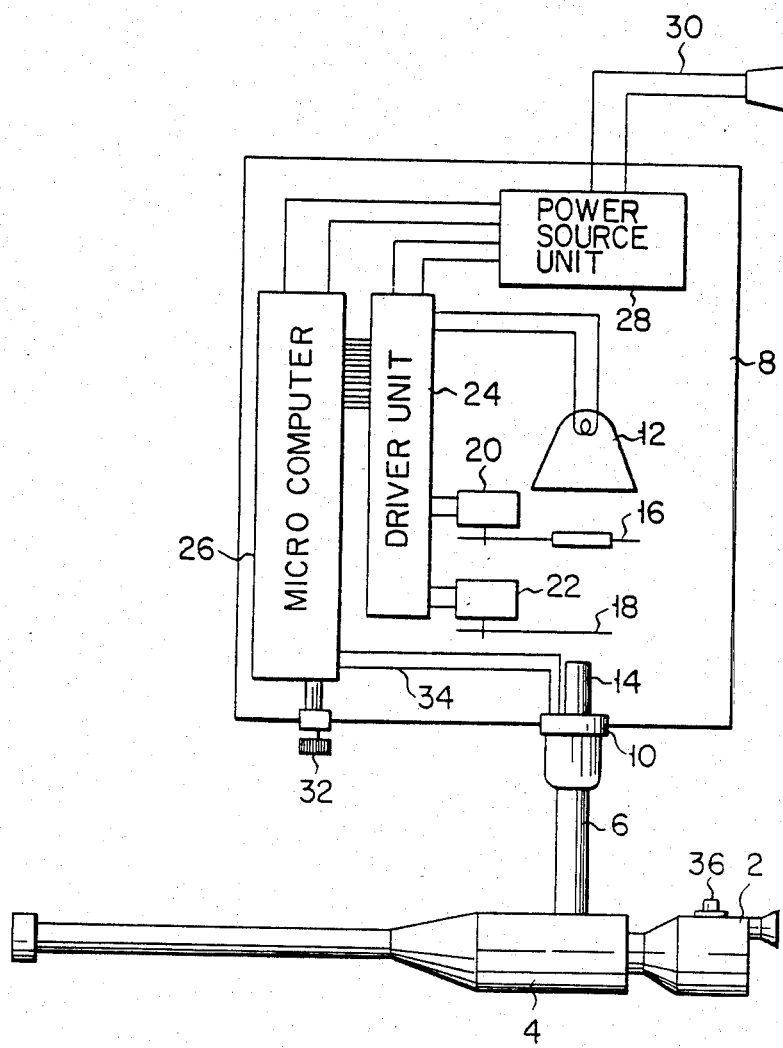

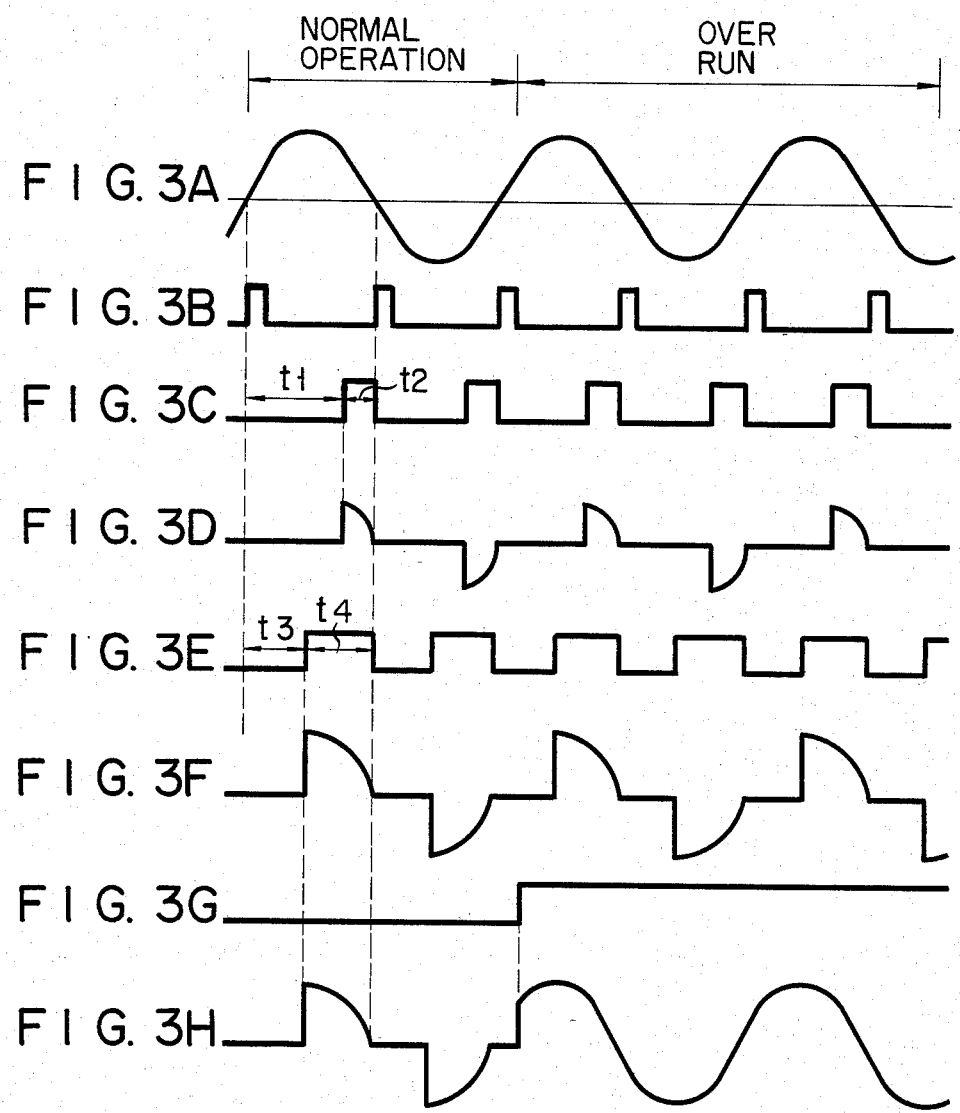

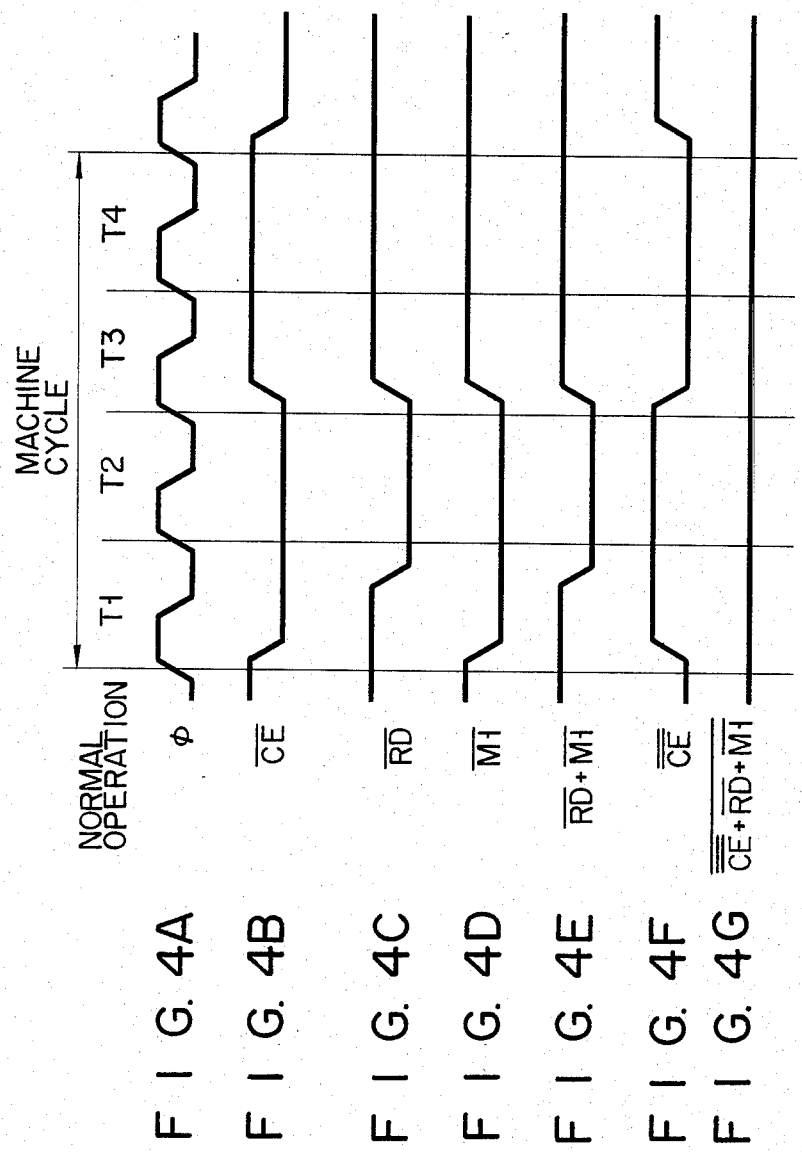

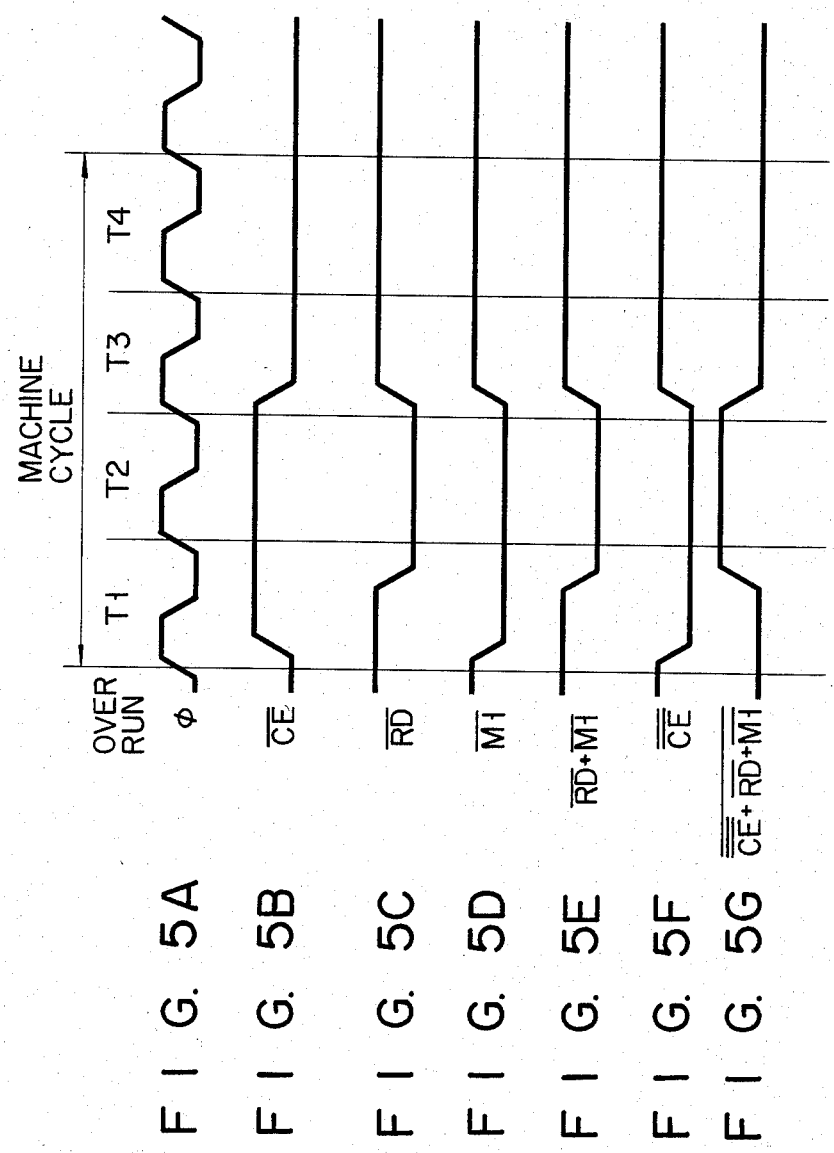

ENDOSCOPE SYSTEM

BACKGROUND OF THE INVENTION

This invention relates to an endoscope system, more specifically to an endoscope system provided with a safety circuit.

Recently, microcomputers have come to be applied to uses in a wide variety of apparatus and systems including endoscope systems. Application of a microcomputer to the use in an endoscope system requires at least the minimum of a safe measure to counter wrong operation of a CPU of the microcomputer due to noise or heat, since the endoscope of the system is used for diagnosis on the human body or the like. Especially in the endoscope with a light source unit, moreover, over run of the CPU will make unstable a lamp current to be supplied to a lamp, or cause a color temperature changing filter or shutter to intercept a light path, thereby preventing a region of interest from being supplied with sufficient illumination light. Thus, it is impossible distinctly to perceive the region of interest through the eyepiece section of the endoscope. This would lead to a security risk.

SUMMARY OF THE INVENTION

The object of this invention is to provide an endoscope system with a CPU ensuring at least the minimum of safety even if case of over run of the CPU.

An endoscope system comprising:

a memory in which control data is stored;

a chip selector for applying a chip enabling signal to the memory to hold the memory in an enabling state in which the control data can be read out from the memory;

means for producing setting signals;

a processor fetching the setting signals as instruction commands and reading out the control data in accordance with the setting signals, said processor having a first terminal from which a first logic signal is delivered while the instruction commands are being fetched, and a second terminal from which a second logic signal is delivered while the control data is being read out from the memory;

a light source;

means for adjusting power supplied to the light source in accordance with the control data;

means for producing an alarm logic signal while the chip selector is not maintaining the memory in the enabling state although the first and second logic signals are being produced; and means for causing the adjusting means to drive the light source at a fixed rate in response to the alarm logic signal.

BRIEF DESCRIPTION OF THE DRAWINGS

FIG. 1 is a schematic view showing an endoscope system according to one embodiment of the invention;

FIGS. 3A to 3H show a timing chart for illustrating the operation of the endoscope shown in FIG. 2;

FIGS. 4A to 4G show a timing chart of a microcomputer in the endoscope system of FIG. 2 when the microcomputer operates normally; and FIGS. 5A to 5G show a timing chart of the micrcomputer when the microcomputer runs over.

DETAILED DESCRIPTION OF THE PREFERRED EMBODIMENT

Figure 2:
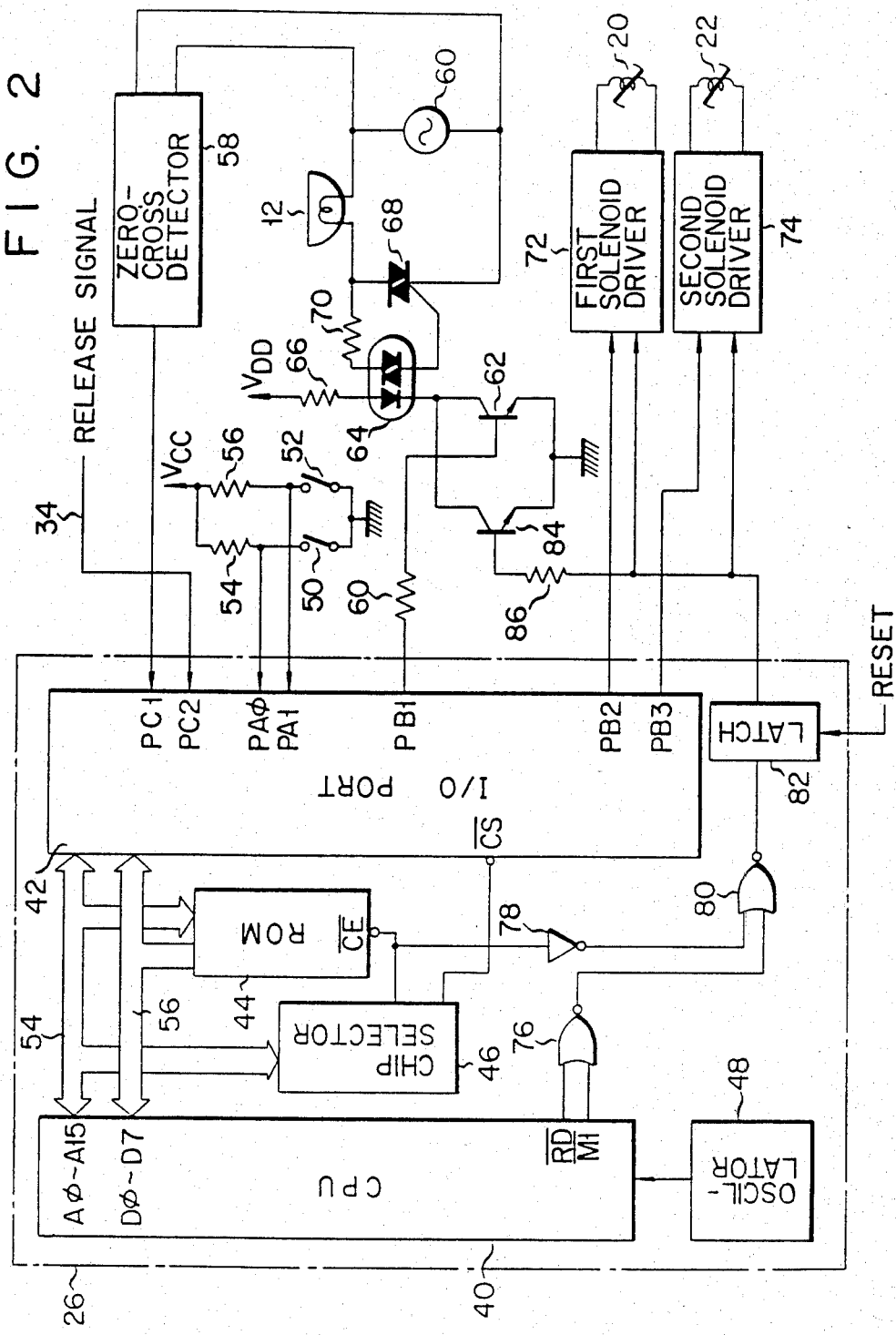
FIG. 2 is a block diagram showing an endoscope system shown in FIG. 1.

FIG. 1 schematically shows an endoscope system. As is generally known, an endoscope camera 2 is attached to the eyepiece section of an endoscope 4, and a universal cord 6 of the endoscope 4 is coupled to the light source unit 8 through a connector 10. Disposed in the light source unit 8 is a lamp 12 to supply illumination light and photographing light to the light incidence surface of a light guide 14 which extends through the universal cord 6. A color temperature changing filter 16 and a shutter 18 are arranged in a light path extending from the lamp 12 to the incidence surface of the light guide 14. The filter 16 and the shutter 18 are coupled to solenoids 20 and 22 to drive them, respectively. The lamp 12 and the solenoids 20 and 22 are connected individually to a driver unit 24, which is connected to a CPU board or microcomputer 26. The driver unit 24 and the CPU board 26 are connected to a power source unit 28 from which extends a power supply cord 30 to be connected to a commercial power source. The CPU board 26 is also connected with a switch unit 32 for setting the brightness of the lamp 12, and is connected to a release signal line 34 which extends from the camera 2 through the universal cord 6.

The microcomputer 26 comprises a CPU 40, an I/O port 42, an ROM 44, a chip selector 46, and an oscillator 48, as shown in FIG. 2. Address terminals $A\phi$ to $A15$ of the CPU 40 are connected to the I/O port 42, the ROM 44, and the chip selector 46 by means of an address bus 54 so that address data are supplied from the CPU 40 to the individual devices. Data terminals $D\phi$ to $D7$ of the CPU 40 are connected to the I/O port 42 and the ROM 44 by means of a data bus 56. Thus, data are read out from the ROM 44 and transmitted to the CPU 40, and data are transferred between the I/O port 42 and the CPU 40.

In a specific circuit arrangement, Z80 (by Zeilog) is used for the CPU 40; 8255A (Programmable I/O by Intel Corp.) for the I/O port 42, 2764 (by Intel Corp.) for the ROM 44, and SN74LS138 (by Texas Instrument Co.) for the chip selector 46. These devices are mounted on an IC base plate.

Input terminals $PA\phi$ and $PA1$ of the I/O port 42 are connected to nodes between lamp brightness setting switches 50 and 52 of a switching unit 32 and resistors 54 and 56, respectively. The resistors 54 and 56 are connected between a power source $V_{CC}$ of a power source unit 28 and the ground. Input terminals PC2 and PC1 of the I/O port 42 are connected, respectively, with the release signal line 34 and a zerocross detector 58 for detecting the zerocross point of AC voltage which is supplied from a commercial AC power source 60 of the power source unit 28. An output terminal PB1 of the I/O port 42 from which a lamp brightness setting signal is delivered is connected to the base of a first transistor 60 through a resistor 62. The emitter of the transistor 60 is grounded, and its collector is connected to a power source $V_{DD}$ through the photodiode of a photocoupler 64 and a resistor 66. The commercial AC power source 60 is connected to a lamp 12 through a Triac 68 for phase-controlling power supplied to the lamp 60. A resistor 70 and the Triac of the photocoupler 64 are connected between the gate of the Triac 68 and a node between the Triac 68 and the lamp 12 so that the Triac 68 is ignited at regular intervals. Output terminals PB2 and PB3 of the I/O port 42 from which a filter insertion signal and a shutter switching signal are delivered, respectively, are connected to solenoid drivers 72 and 74, respectively. The solenoid drivers 72 and 74 are connected to the solenoids 20 and 22 for filter and shutter, respectively.

The chip selector 46 is connected to the chip selecting terminal $\overline{CS}$ of the I/O port 42 and the chip enabling terminal $\overline{CE}$ of the ROM 44, and the CPU 40 selects a chip in accordance with an instruction code. The memory readout signal terminal $\overline{RD}$ and machine cycle signal terminal $\overline{M1}$ of the CPU 2 are connected to an OR gate 76. The output of the OR gate 76 and the output of an inverter 78 connected to a chip enabling signal line are connected to a NOR gate 80, whose output is connected to a latch 82. The output of the latch 82 is connected to the base of a second transistor 84 through a resistor 86 and the solenoid drivers 72 and 74. The collector and emitter of the second transistor 84 are connected between the photodiode of the photocoupler 64 and the ground.

Constructed in this manner, the embodiment of this invention shown in FIGS. 1 and 2 operates as follows. When commercial AC supply voltage is supplied to the zerocross detector 58, as shown in FIG. 3A, the zerocross detector 58 detects the zerocross point, and produces a zerocross signal as shown in FIG. 3B. The produced zerocross signal is applied to the input terminal PC1 of the I/O port 42. Thereupon, when the lamp brightness setting switch 50 is closed, a low-level signal is supplied to the input terminal PA$\phi$ of the I/O port 42. The low-level signal and the zerocross signal are fetched as instruction codes to the CPU 26 through the data bus 54. In response to the fetched instruction codes for lamp control, the CPU 40 causes the chip selector 46 to select the ROM 44 in which data for lamp control is stored and the I/O port 42 for lamp control. Thus, in response to an instruction code, prescribed data, i.e., data for a delay time t1, is read out from the ROM 44 with a prescribed address. The data read out in this manner is transferred from the ROM 44 to the selected I/O port 42. As a result, a low-level signal is delivered from the output terminal PB of the I/O port 42 for the delay time t1 starting from a zerocross point, as shown in FIG. 3C, and then a high-level signal is delivered for a time t2 directly following the time t1 and ending at the next zerocross point. Accordingly, the first transistor 62 is off for the delay time t1 and is on for the time t2. During the time t2 when the first transistor 62 is on, the photodiode of the photocoupler 64 emits light, and the photo-Triac of the photocoupler 64 is turned on to turn on the Triac 64. As a result, the lamp 12 is supplied with power from the AC power source 60 for the time t2. Thus, a current as shown in FIG. 3D is continuously supplied to the lamp 12 so that the lamp 12 glows with proper brightness. In this manner, sufficient illumination light can be supplied to the light guide 14 to secure satisfactory illuminated diagnosis. In the illuminated diagnosis, a filter removal signal and a shutter opening signal are applied from the CPU 40 to the output terminals PB2 and PB3, respectively, of the I/O port 42 to keep the solenoids 20 and 22 nonoperating, thereby removing the filter 16 and the shutter 19 from the light path.

If the light source brightness setting switch 52 is closed instead of the switch 50, a delay time t3 is read out from the ROM 44 in place of the delay time t1, and an output signal as shown in FIG. 3E is delivered from the output terminal PB1 of the I/O port 42. Thus, a current as shown in FIG. 3F is supplied to the lamp 12 to secure modified proper light source brightness, e.g., higher brightness.

The CPU 40 can decide whether the frequency of the AC power source is 50 Hz or 60 Hz by counting zerocross signals as shown in FIG. 3B. A proper delay time is selected from data in the ROM 44 on the basis of the decision. Thus, whether the frequency is 50 Hz or 60 Hz, the lamp 12 can be turned on to glow with specified brightness.

In photographing, when a release button 36 of the camera 2 is depressed, a synchro signal is applied to the input terminal PC2 of the I/O port 42 through the release signal line 34. When supplied with the synchro signal, the CPU 26 applies a filter insertion signal to the output terminal PB2 of the I/O port 42, and actuates the solenoid driver 72 to drive the solenoid 20, thereby locating the filter 16 in the light path. When the filter 16 is located in the light path, a mirror shutter (not shown) of the camera 2 is opened, and a film set in the camera 2 starts to be exposed. If the camera 2 includes a photometer, a shutter closing signal is applied from the CPU 26 to the output terminal PB3 of the I/O port 42 in response to an exposure stop signal delivered from the photometer. If the camera 2 is so designed that its exposure time is externally manually set, the shutter closing signal is applied after the passage of a programmed delay time. Accordingly, the solenoid driver 74 is actuated to drive the solenoid 22, thereby locating the shutter 18 in the light path. Thus, film exposure is completed. When the mirror shutter of the camera 2 is closed, the filter 16 and the shutter 18 are removed from the light path to their original positions.

Referring now to FIGS. 3A to 3G and 4A to 4G, there will be described timings of the CPU 40 for cases where the CPU 40 operates normally and where it runs over due to noise or heat. FIGS. 4A to 4G show timings in a machine cycle to fetch instruction codes. The CPU 40 is supplied with basic clock pulses as shown in FIG. 4A from the oscillator 48. A chip selecting signal is applied from the chip selector 46 to the chip selecting terminal $\overline{CS}$ of the I/O port 42. If the chip selecting signal goes low, the I/O port 42 is selected, and the I/O gate of the I/O port 42 is opened. Accordingly, an instruction code is fetched from the I/O port 42 to the CPU 40 through the data bus 13. A chip selecting signal as shown in FIG. 4B is applied from the chip selector 46 to the chip enabling terminal $\overline{CE}$ of the ROM 44. If this chip selecting signal goes low, the ROM 44 is selected and held ready for readout. Accordingly, an instruction code is fetched from the ROM 44 to the CPU 40 with a prescribed address. At this time, the memory readout terminal $\overline{RD}$ is maintained at low level, as shown in FIG. 4C. When the instruction code is fetched to the CPU 40, the machine cycle signal terminal $\overline{M1}$ is also maintained at low level, as shown in FIG. 4B. Therefore, while the output of the OR gate 76 is at low level, as shown in FIG. 4E, the CPU 40 reads instructions. Meanwhile, if the chip enabling terminal $\overline{CE}$ of the ROM 44 is at low level, data is read from the ROM 44. Thus, the output of the inverter 78 is as shown in FIG. 4F. As the outputs of the inverter 78 and the OR gate 76 are supplied to the NOR gate 80, the output of the NOR gate 80 is maintained at low level, as shown in FIG. 4G, and the second transistor 84 is kept off. Moreover, the solenoid drivers 72 and 74 are prevented from being returned to the nonoperating state by the output of the NOR gate 80. In this state, current supply to the lamp 12 is controlled in accordance with the on-off operation of the first transistor 62, and the solenoid drivers 72 and 74 are controlled by outputs from the output terminals PB2 and PB3 of the I/O port 42.

If the CPU 40 run over, then the CPU 40 will fetch instruction data from some other memory region than the ROM 44. Namely, the chip selector 46 selects an empty region (e.g., a spare region for an additional ROM) on the CI substrate on which some other chip than the ROM 44 is to be mounted, and instruction data is fetched from the empty region to the CPU 40. In other words, a high-level non-enabling signal as shown in FIG. 5B is applied to the chip enabling terminal $\overline{CE}$ of the ROM 44, and instruction data is fetched to the CPU 40 also in a period during which the ROM 44 is not selected. Thus, the terminals $\overline{RD}$ and $\overline{M1}$ of the CPU 40 are maintained at low level, as shown in FIGS. 5C and 5D. Accordingly, the outputs of the inverter 78 and the OR gate 76 are kept at low level, as shown in FIGS. 5F and 5E, respectively, and a high-level signal is delivered from the NOR gate 80, as shown in FIG. 5G. This high-level signal is maintained by the latch 82. As a result, a high-level signal as shown in FIG. 5G is applied to the second transistor 84 and the solenoid drives 72 and 70. Thus, the second transistor 84 is turned on to keep the Triac 64 in conduction and the solenoid drivers 72 and 74 nonoperating, and the lamp 12 is supplied with an AC current which is not phase-controlled, as shown in FIG. 3H, so that the lamp 12 is turned on to glow with maximum brightness. If the shutter 18 or the filter 16 is located in the light path, therefore, it is removed from the path to allow illumination light to be securely supplied to the region of interest.

When an operator notices the run over of the microcomputer, he is to stop the operation of the system after suspending endoscopic diagnosis or treatment. At this time, if the operator depresses a reset button, a reset signal is applied to the latch 82 to clear the same.

It is to be understood that the lamp 12 may glow not with the maximum brightness but with limited brightness.

According to the aforementioned embodiment, the illumination light continues to be supplied from the light source for the endoscope to the light guide even if the CPU runs over, so that a satisfactory visual field may be secured in the endoscope system.

Thus, according to this invention, there may be provided an endoscope system with high safety.

What is claimed is:

1. An endoscope system comprising:
   a memory for storing control data;
   a chip selector operatively connected to said memory for applying a chip enabling signal to the memory to hold the memory in an enabling state in which the control data can be read out from the memory;
   means for producing setting signals;
   a processor operatively connected to said means, for fetching the setting signals as instruction commands, operating the chip selector and reading out the control data from the memory in response to the setting signals when the memory is maintained in the enabling state by the chip selector;
   a light source in said endoscope system;
   means operatively connected to the light source for adjusting power supplied to the light source in response to the receipt of the control data;
   means for producing an alarm signal while the memory is not maintained in the enabling state by the chip selector which is operated under the control of the processor although the setting signals are being produced; and
   means operatively connected to said alarm signal producing means for causing the adjusting means to operate the light source at a fixed brightness in response to the alarm system.

2. An endoscope system according to claim 1, wherein said processor has a first terminal from which a first logic signal is delivered while the instruction commands are fetched, and a second terminal from which a second logic signal is delivered while the control data is read out from the memory, and wherein said alarm signal producing means produces the alarm signal when the processor does not erroneously cause the chip selector to maintain the memory in the enabling state although the first and second logic signals are being produced.

3. The endoscope system according to claim 1, wherein said means for producing the setting signals includes means for discriminating power supply frequency and a switching circuit.

4. The endoscope system according to claim 1, wherein said means for producing the alarm signal includes a logic circuit including a latch circuit for latching the alarm signal.

5. The endoscope system according to claim 1, wherein said means for causing the light source adjusting means to operate the light source includes a switching element to be closed in response to the alarm signal.

6. The endoscope system according to claim 1 further comprising a shutter capable of being located in a light path through which light from the light source passes, and means for removing the shutter from the source light path in response to an alarm signal.

7. The endoscope system according to claim 1, further comprising a filter capable of being located in a light path through which light from the light source passes, and means for removing the filter from the light path in response to an alarm signal.

* * * * *